(12) United States Patent
Aylsworth et al.

(10) Patent No.: US 7,007,694 B2
(45) Date of Patent: Mar. 7, 2006

(54) NASAL CANNULA

(75) Inventors: Alonzo C. Aylsworth, Wildwood, MO (US); Charles R. Aylsworth, Wildwood, MO (US); Lawrence C. Spector, Austin, TX (US)

(73) Assignee: Acoba, LLC, Chesterfield, MO (US)

( * ) Notice: Subject to any disclaimer, the term of this patent is extended or adjusted under 35 U.S.C. 154(b) by 0 days.

(21) Appl. No.: 11/053,587

(22) Filed: Feb. 8, 2005

(65) Prior Publication Data

US 2005/0257794 A1 Nov. 24, 2005

Related U.S. Application Data

(60) Provisional application No. 60/573,566, filed on May 21, 2004.

(51) Int. Cl.
*A61M 16/00* (2006.01)
*A61M 15/08* (2006.01)

(52) U.S. Cl. .............................. 128/206.11; 128/207.18
(58) Field of Classification Search ........... 128/206.11, 128/205.25, 203.22, 205.27, 205.29, 206.12, 128/206.16, 206.18, 206.29, 207.18; 600/529–533
See application file for complete search history.

(56) References Cited

U.S. PATENT DOCUMENTS

| | | | | | |
|---|---|---|---|---|---|
| 2,931,358 | A | * | 4/1960 | Sheridan | 128/207.18 |
| 4,278,082 | A | * | 7/1981 | Blackmer | 128/207.18 |
| 5,046,491 | A | * | 9/1991 | Derrick | 128/200.24 |
| 5,113,857 | A | * | 5/1992 | Dickerman et al. | 128/207.18 |
| 5,137,017 | A | * | 8/1992 | Salter | 128/207.18 |
| 5,509,409 | A | | 4/1996 | Weatherholt | |
| 5,533,506 | A | | 7/1996 | Wood | |
| 6,155,986 | A | * | 12/2000 | Brydon et al. | 600/538 |
| 6,213,955 | B1 | * | 4/2001 | Karakasoglu et al. | 600/529 |
| 6,298,850 | B1 | | 10/2001 | Argraves | |
| 6,439,234 | B1 | * | 8/2002 | Curti et al. | 128/207.18 |
| 6,478,026 | B1 | * | 11/2002 | Wood | 128/207.18 |
| 6,655,385 | B1 | | 12/2003 | Curti et al. | |
| 6,679,265 | B1 | | 1/2004 | Strickland et al. | |
| 6,684,883 | B1 | * | 2/2004 | Burns | 128/207.18 |
| 6,763,832 | B1 | * | 7/2004 | Kirsch et al. | 128/207.18 |
| 6,776,163 | B1 | | 8/2004 | Dougill et al. | |
| 6,783,573 | B1 | * | 8/2004 | Richardson | 96/6 |
| 6,799,575 | B1 | | 10/2004 | Carter | |
| 2002/0122746 | A1 | * | 9/2002 | Yamamori et al. | 422/83 |
| 2003/0111081 | A1 | * | 6/2003 | Gupta | 128/207.18 |
| 2005/0066976 | A1 | * | 3/2005 | Wondka | 128/207.18 |

* cited by examiner

*Primary Examiner*—Teena Mitchell
(74) *Attorney, Agent, or Firm*—Mark E. Scott; Conley Rose PC

(57) ABSTRACT

A nasal cannula. Some illustrative embodiments are a cannula comprising a first nasal tube having a device end and an aperture end (the cannula configured to place the aperture end in fluid communication with the first naris of a patient), a second nasal tubing having a device end and an aperture end (the cannula configured to place the aperture end of the second nasal tubing in fluid communication with a second naris of the patient), and an oral tubing having a device end and an aperture end, and the oral tubing mechanically coupled to at least one of the first or second nasal tubing (the cannula configured to place the aperture end of the oral tubing in fluid communication with the mouth of a patient). The first nasal tubing, the second nasal tubing and the oral tubing are fluidly independent between their aperture ends and their device ends.

12 Claims, 6 Drawing Sheets

NASAL CANNULA

CROSS-REFERENCE TO RELATED APPLICATIONS

This specification claims the benefit of provisional application Ser. No. 60/573,566 filed May 21, 2004, titled, "Three Tube Cannula," which application is incorporated by reference herein as if reproduced in full below.

STATEMENT REGARDING FEDERALLY SPONSORED RESEARCH OR DEVELOPMENT

Not applicable.

BACKGROUND OF THE INVENTION

1. Field of the Invention

Embodiments of the invention are directed to nasal and oro-nasal cannulas.

2. Description of the Related Art

Related art cannulas come in several varieties. A "single lumen" cannula provides a single fluid connection from a patient's nares to a respiratory device, such as an oxygen concentrator. Each piece of tubing extending over a patient's ears fluidly merge, such as under the patient's chin or behind the patient's head. Thus, in a single lumen cannula only a single flow path exists between the patient and a respiratory device in spite of the fact that the cannula may have two nasal prongs, one for each naris. "Dual lumen," "bifurcated" or divided nasal cannulas have to two independent flow paths, one each for each naris of a patient. Much like the single lumen cannula, a dual lumen cannula may have two nasal prongs. In a dual lumen cannula, however, the flow pathways to each naris may be separated by a barrier or bifurcation.

Nasal cannulas of any variety are a very personal item, and not generally shared with others. In fact, sharing of a nasal cannula could result in a transmission of various ailments from person to person, such as tuberculosis. The respiratory devices to which the cannulas connect may also pose a risk of transmitting various ailments. For example, a conserver device, which senses inhalation of a patient and delivers a bolus of therapeutic gas, may be transferred from patient to patient. Even if a new nasal cannula is used for each patient, the conserver may carry viruses and/or bacteria from one patient to the next. This risk is minimal for respiratory devices where patient airflow does not flow through the device.

At least some of the inventors of the present specification, however, have developed technology related to various aspects of nasal and/or oro-nasal airflow sensing where the patient's respiratory airflow, at least in part, flows through the respiratory device. For example, U.S. patent application Ser. No. 10/616,042, titled "Method and System For Measuring Air Flow of Nares" describes, in some embodiments, using mass flow sensors as the mechanism to detect nasal and/or oro-nasal respiration. U.S. patent application Ser. No. 10/697,232, titled "Method and System of Sensing Air Flow and Delivering Therapeutic Gas to a Patient" describes, in some embodiments, using mass flow sensors to sense nasal and/or oro-nasal respiration and the delivery of therapeutic gas based on those individual measurements. Finally, U.S. patent application Ser. No. 10/850,496, titled "Method and System to Determine Nasal Resistance to Air Flow" describes, in some embodiments, using mass flow sensors to determine values indicative of a patient's nasal resistance. In each of these applications, a portion of the patient's exhaled airflow passes through the nasal cannula and the respiratory device performing the measurements. Thus, if the respiratory devices are used by multiple patients, they run the risk of becoming a vehicle for the transfer of various viruses and/or bacteria. Moreover, many of the devices developed by at least some of the inventors of the present specification need to measure airflow and/or pressure of each breathing orifice individually, but these measurements are difficult using related art single lumen and/or dual lumen nasal cannulas, especially with regard to oro-nasal measurements.

SUMMARY OF SOME OF THE PREFERRED EMBODIMENTS

The problems noted above are solved in large part by improved nasal cannulas. Some illustrative embodiments are a cannula comprising a first nasal tube having a device end and an aperture end (wherein the cannula is configured to place the aperture end in fluid communication with the first naris of a patient), a second nasal tubing having a device end and an aperture end (wherein the cannula is configured to place the aperture end of the second nasal tubing in fluid communication with a second naris of the patient), and an oral tubing having a device end and an aperture end, and the oral tubing mechanically coupled to at least one of the first or second nasal tubing (wherein the cannula is configured to place the aperture end of the oral tubing in fluid communication with the mouth of a patient). The first nasal tubing, the second nasal tubing and the oral tubing are fluidly independent between their aperture ends and their device ends.

Other illustrative embodiments may be a cannula comprising a first nasal tubing (wherein the cannula is configured to place a patient end of the first nasal tubing in fluid communication with a first naris of a patient), a first inline filter within the flow path of the first nasal tubing, a second nasal tubing mechanically coupled to the first nasal tubing (wherein the cannula is configured to place a patient end of the second nasal tubing in fluid communication with the second naris of the patient), and a second inline filter within the flow path of the second nasal tubing. The first and second nasal tubings are fluidly independent.

Yet further illustrative embodiments may be a respiratory air filter comprising a first flow pathway comprising an inlet port and an outlet port fluidly coupled to a first cavity (the first cavity defined, at least in part, by an outer housing), a second flow pathway comprising an inlet port and an outlet port fluidly coupled to a second cavity (the second cavity defined, at least in part, by an outer housing), a first filter within the first cavity, and a second filter within the second cavity. At least a portion of the outer housing defining the first cavity is mechanically coupled to the outer housing defining the second cavity.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the various embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

Figure 1:
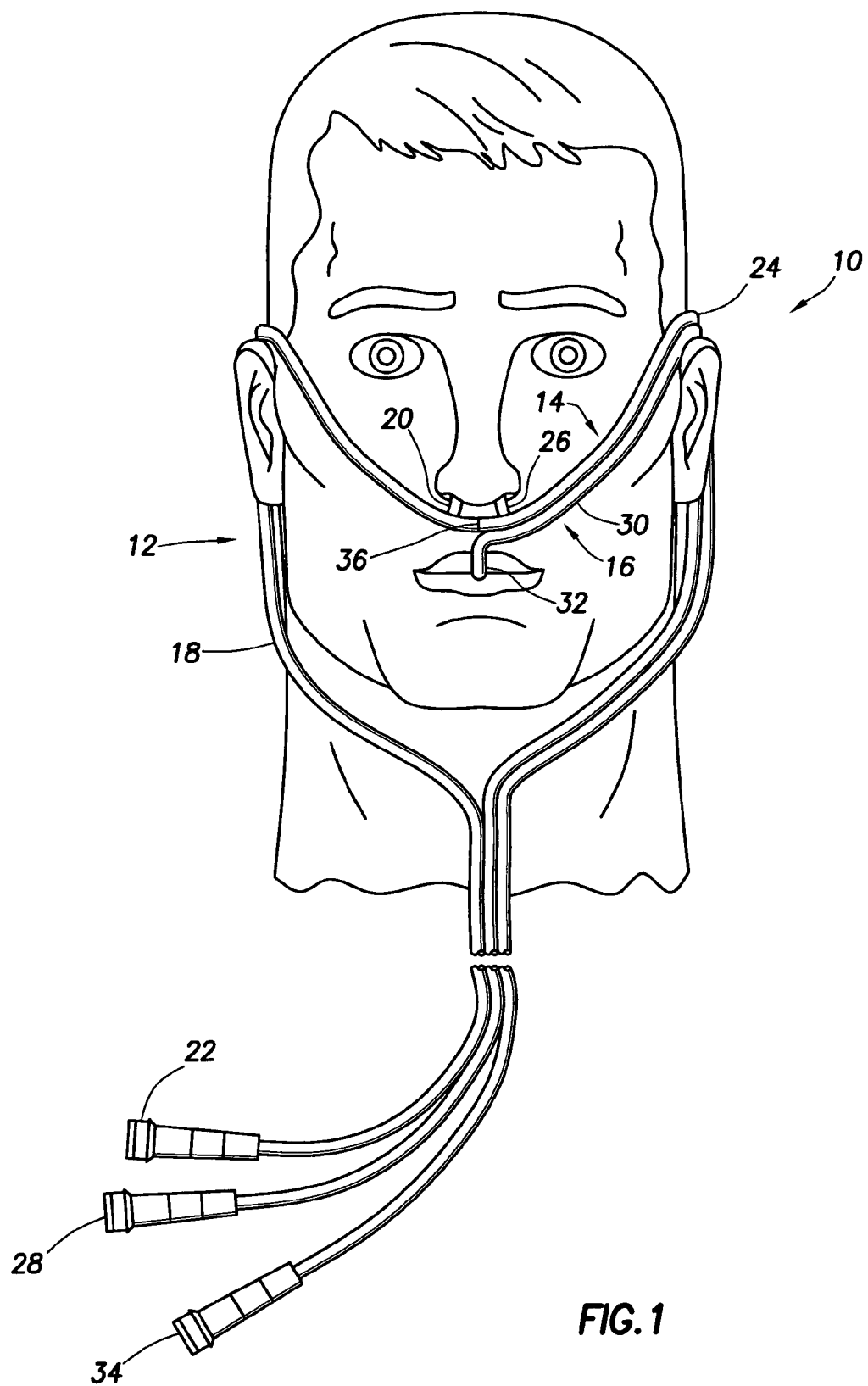
FIG. 1 illustrates a three tube cannula assembly in accordance with embodiments of the invention.

FIG. 1 illustrates a three tube cannula assembly 10 comprising a first nasal tubing assembly 12, a second nasal tubing assembly 14, and an oral tubing assembly 16. First nasal tubing assembly 12 comprises a tube 18 having a nasal interface or prong 20 on the aperture or patient end, and a connector 22 on a device end. Second nasal tubing assembly 14 comprises a tube 24 having a nasal prong 26 on the aperture or patient end, and a connector 28 on a device end. Oral tubing assembly 16 comprises tube 30 having an oral interface 32 on the aperture or patient end, and a connector 34 on the device end. Each tubing assembly 12, 14 and 16 provides an independent and isolated fluid flow pathway from their patient interfaces (nasal prongs 20, 26 and oral interface 32) to their connectors 22, 28 and 34 through their respective tubing, which tubing may have an inner diameter approximately equal to 1/16 inch in some embodiments.

Still referring to FIG. 1, nasal tubing assemblies 12 and 14 are mechanically connected near the prongs 20 and 26, although they are not in fluid communication with each other. In particular, in some embodiments a permanent barrier or bifurcation 36 fluidly isolates the tubings 18 and 24. With respect to the relationship of oral tubing and nasal tubing, oral tubing 30 runs parallel to nasal tubing 24. In accordance with embodiments of the invention, the oral tubing is mechanically coupled to the illustrative nasal tubing 24, such as by a bonding agent, or mechanical device or devices that hold the two tubings together. FIG. 1 shows the oral tubing 30 hooked behind the patient's left ear, through oral tubing 30 may equivalently run parallel to the nasal tubing 18 over the patient's right ear. Although the illustrative FIG. 1 shows the nasal tubings 18 and 24, along with the oral tubing 30, converging below the patient's chin, the convergence point may be equivalently behind the patient's head (not specifically shown).

The illustrative three tube cannula assembly 10 of FIG. 1 may be used, for example, in individually measuring attributes of airflow through each of a patient's breathing orifices, such as described in co-pending U.S. patent application Ser. No. 10/616,042, titled "Method and System for Measuring Air Flow of Nares," filed Jul. 9, 2003 and incorporated by reference herein as if reproduced in full below. In embodiments of these devices which individually sense an attribute of airflow for each of the patient's breathing orifices, the illustrative three tube cannula assembly 10 provides a convenient mechanism for fluidly coupling the various orifices to the illustrative respiratory devices by way of a single, integral assembly 10 not heretofore seen or contemplated in the related art.

Figure 2:
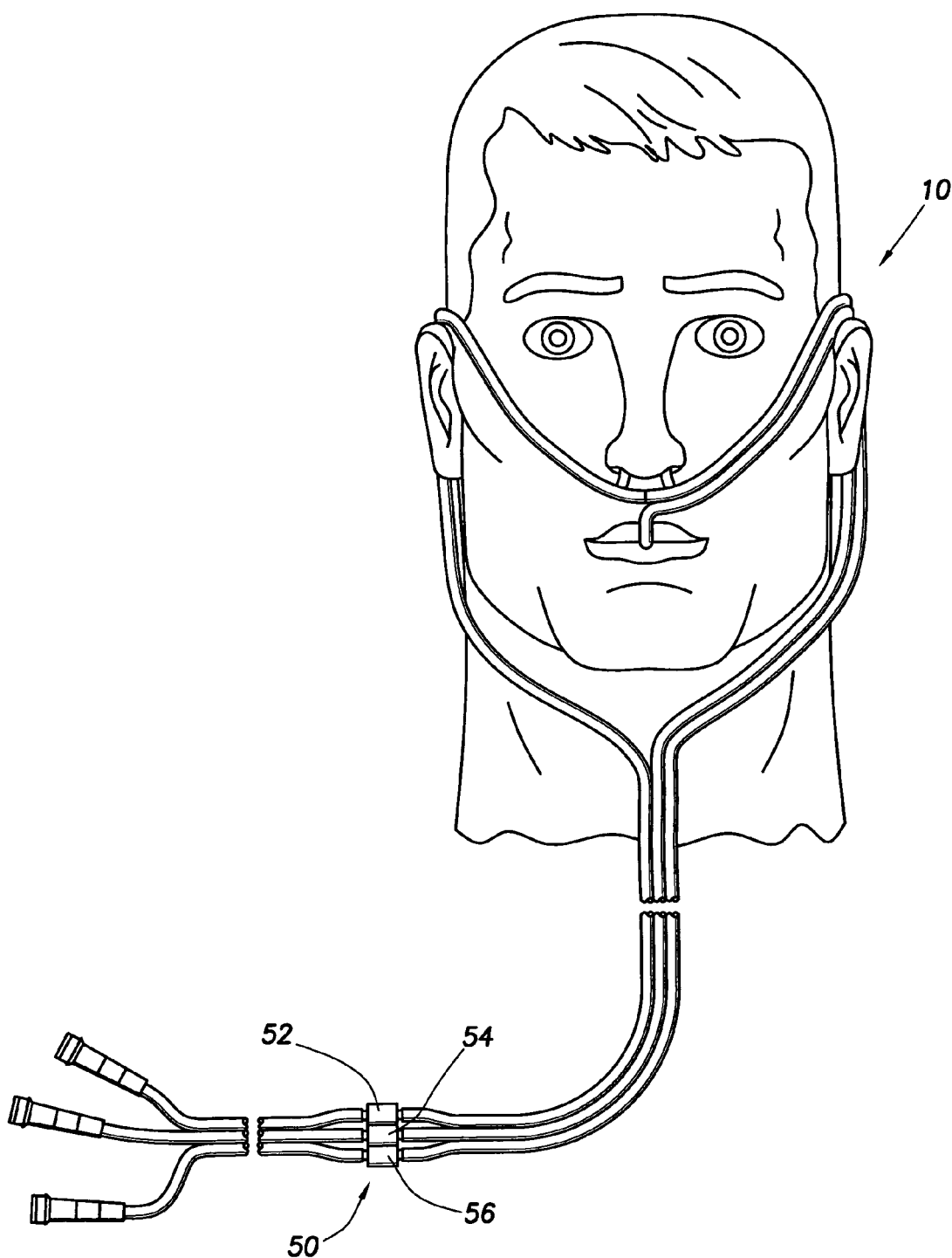
FIG. 2 illustrates alternative embodiments of a three tube cannula assembly in accordance with embodiments of the invention.

FIG. 2 illustrates alternative embodiments of the three tube cannula assembly 10 that comprises an integral filter assembly 50 fluidly coupled within each of the flow pathways of the three tube cannula assembly 10. In particular, in the embodiments illustrated in FIG. 2 the integral filter assembly 50 comprises a first filter assembly 52, a second filter assembly 54 and a third filter assembly 56. Each of the filter assemblies may comprise a microbial and/or hydrophobic filter element. Illustrative embodiments of an integral filter assembly 50 are discussed more fully with respect to FIG. 7. FIG. 2, however, illustrates that in accordance with at least some embodiments of the invention, each tube of the three tube cannula assembly 10 comprises its own filter inline with the fluid flow pathway, fluidly independent from the fluid flow pathways of the other tubes and other filters. Devices that use mass flow sensors (where the patient's respiratory exhalation flows through the device) are protected from becoming carriers of viruses and/or bacteria, as the viruses and/or bacteria are kept out of the devices by way of the filters. Likewise, to the extent the device to which an illustrative three tube cannula assembly 10 is connected carries viruses and/or bacteria, the microbial filter ensures that these microbes are not inhaled by the patient.

Figure 3:
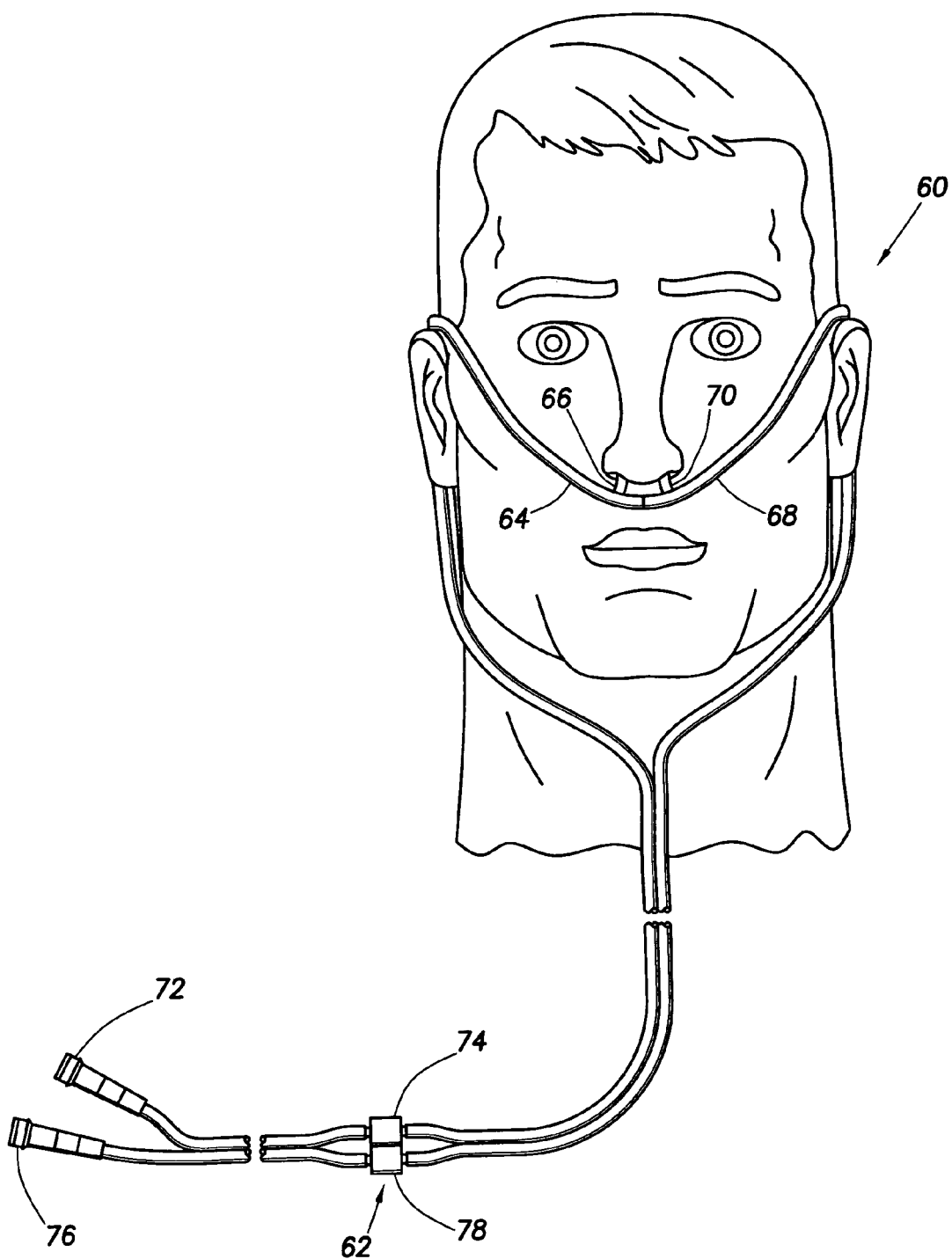
FIG. 3 illustrates alternative embodiments comprising a dual lumen cannula in accordance with embodiments of the invention.

There may be situations where measuring an attribute of oral airflow is not needed, yet the protection of a filter may still be needed. FIG. 3 illustrates alternative embodiments of the invention comprising a dual lumen or bifurcated cannula assembly with an integral filter assembly 62 coupled within the fluid flow pathway. In particular, the illustrative bifurcated nasal cannula comprises a first tubing 64 fluidly coupled within the patient's right naris by way of a nasal prong 66. Likewise, the bifurcated nasal cannula 60 comprises a second tubing 68 coupled to the patient's left naris by way of a second nasal prong 70. The tubing 64 and nasal prong 66 are in fluid communication with the connector 72 through a first filter assembly 74 of the illustrative integral filter assembly 62. Likewise, the second tubing 68 and corresponding nasal prong 70 are in fluid communication with the connector 76 by way of a second filter assembly 78, being part of the integral filter assembly 62. Each of the filter assemblies 74, 78 may comprise a microbial and/or hydrophobic filter element.

Figure 4:
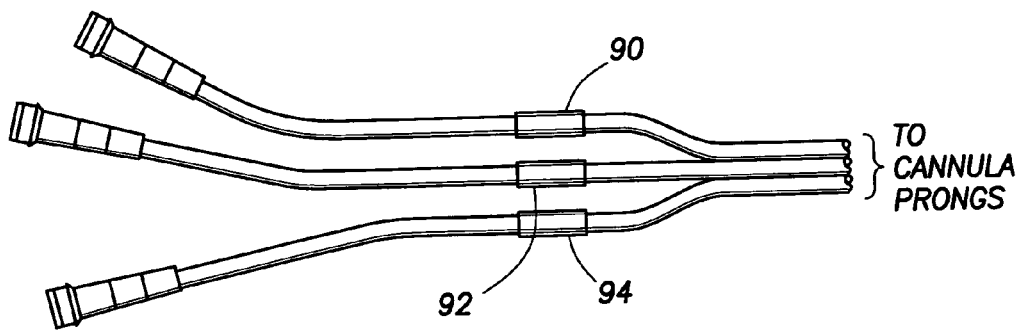
FIG. 4 illustrates non-integral filter assemblies in accordance with embodiments of the invention.
Figure 5:
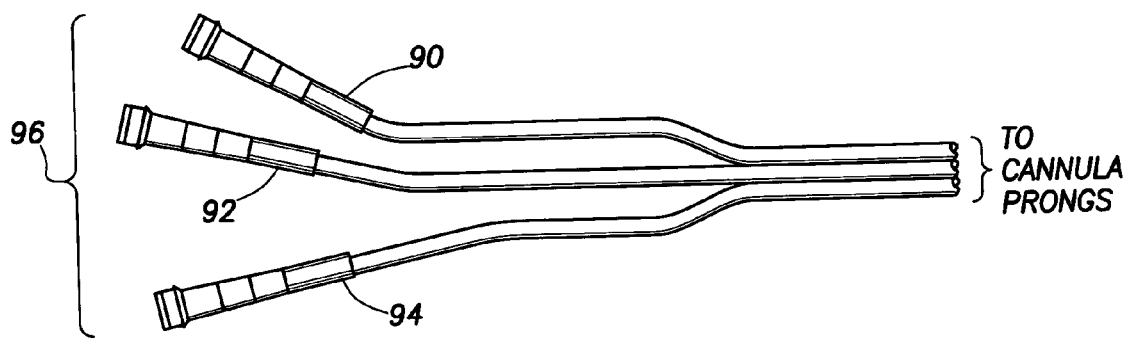
FIG. 5 illustrates non-integral filter assemblies in accordance with alternative embodiments of the invention.
Figure 6:
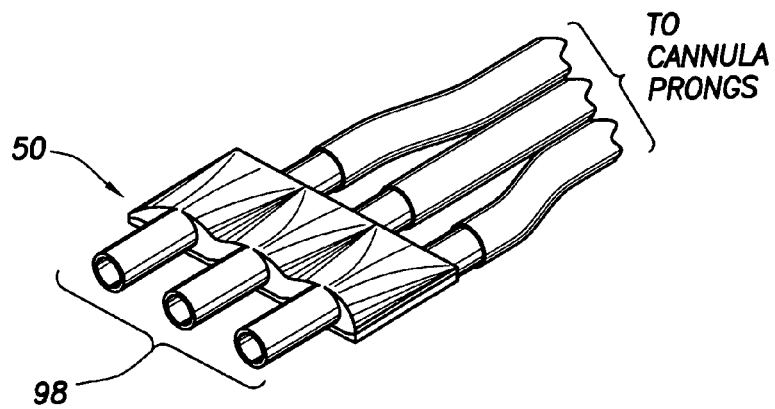
FIG. 6 illustrates an integral filter assembly in accordance with embodiments of the invention.

In the illustrative embodiments of FIGS. 2 and 3, filter assemblies are shown to be integral units placed between a patient end and a device end of the nasal cannula, the device end comprising the connectors. FIG. 4 illustrates alternative embodiments of the invention comprising non-integral filter assemblies. In particular, FIG. 4 illustrates, for the case of a three tube cannula assembly, a first filter assembly 90, a second filter assembly 92, and a third filter assembly 94. FIG. 4 thus illustrates that the filters need not necessarily be an integral unit with fluidly divided cavities containing microbial and/or hydrophobic filter elements. In the illustrative embodiments of FIG. 4, however, each of the filter assemblies 90, 92 and 94 are shown to be between the patient end of the nasal cannula and the device end. In illustrative FIG. 5, the non-integral filter assemblies 90, 92 and 94 may be proximate to connectors, generically labeled 96. In fact, in these embodiments each of the filter assemblies 90, 92 and 94 may be integral with their respective connectors, and thus at least in part form the device end of the cannula. FIG. 6 illustrates yet further alternative embodiments wherein an integral filter assembly 50 may itself perform a dual function of filtering the air and being a connector by which the nasal cannula couples to respiratory devices. In particular, the illustrative three ports 98 of FIG. 6 may plug directly into an illustrative device, such as a device to determine nasal resistance, without the need of further tubing and/or connectors. Although FIGS. 4, 5 and 6 show three independent flow pathways, and thus are applicable for a three tube cannula assembly 10, the descriptions are equally applicable for a bifurcated nasal cannula, such as illustrative bifurcated cannula 60 of FIG. 3.

Figure 7:
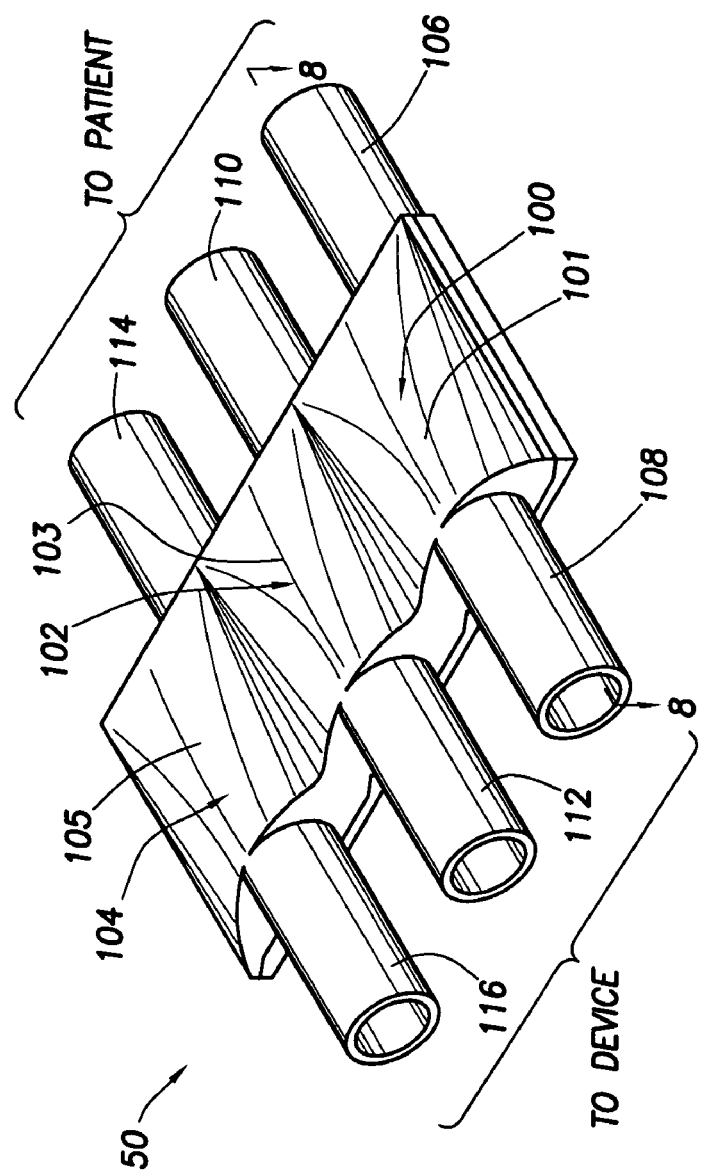
FIG. 7 illustrates, in greater detail, an integral filter assembly in accordance with embodiments of the invention.

Turning now to FIG. 7, an illustrative integral filter assembly 50 is discussed in greater detail. The integral filter assembly 50 comprises three fluidly isolated cavities 100, 102 and 104 defined, respectively, by three outer housings 101, 103 and 105. Each cavity fluidly couples to an inlet port, which couples to the patient, and an outlet port, which couples to a sensing device. However, in some situations respiratory airflow moves both in and out of each port, and the labels of "inlet port" and "outlet port" are merely for purposes of distinguishing the various ports. Cavity 100 is fluidly coupled to an inlet port 106 and an outlet port 108. Likewise, cavity 102 is fluidly coupled to an inlet port 110 and an outlet port 112. Finally, cavity 104 is fluidly coupled to inlet an port 114 and an outlet port 116. In accordance with at least some embodiments of the invention, the inlet ports 106, 110 and 114 are coplanar. Likewise, the outlet ports 108, 112 and 116 are coplanar, and the planes defined by the inlet ports and the outlet ports are substantially parallel.

Figure 8:
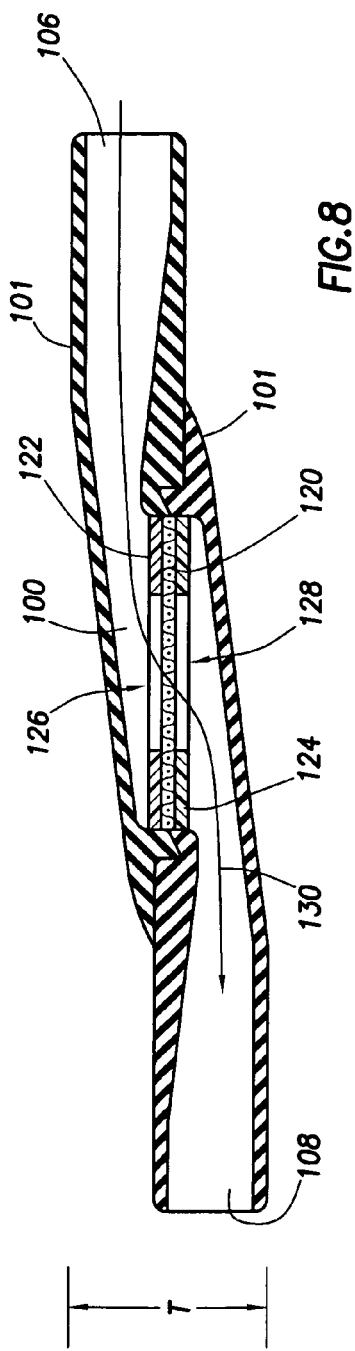
FIG. 8 shows an elevational cross-sectional view of a filter assembly taken along line 8—8 of FIG. 7.

FIG. 8 illustrates a cross-sectional elevational view of a cavity and corresponding inlet and outlet ports taken along line 8—8 of FIG. 7. Thus, FIG. 8 is discussed in relation to cavity 100 defined by outer housing 101; however, it will be understood that the discussion is equally applicable to the flow pathways through cavities 102 and 104. In particular, cavity 100 fluidly couples to inlet port 106 and outlet port 108. The cavity 100 is bisected or divided by a hydrophobic and/or microbial filter 120, and thus the airflow through inlet port 106 and outlet port 108 (in either direction) flows through the filter 120. For example, during exhalation of a patient, airflow may move through the filter assembly in the direction indicated by arrow 130. During inhalation, the airflow may be reversed. The filter 120 may be any suitable material for filtering moisture, bacteria and/or viruses, such as filter material provided by Whatman International, Ltd. of Maidstone, England or Porous Media of St. Paul, Minn. The filter material 120 may be held in place by internal members 122 and 124, each having at least one aperture 126 and 128 respectively therethrough. The apertures allow airflow through the filter.

Referring to FIGS. 7 and 8 somewhat simultaneously, it is seen that the plane defined by the filter material 120 may be substantially parallel to a plane defined by the inlet ports. Likewise, the filter material 120 may be substantially parallel to a plane defined by the outlet ports 108. While aligning the filter material 120 in a plane substantially parallel to a plane defined by the inlet ports and outlet ports is not strictly required to practice embodiments of the invention, such an alignment reduces the thickness "T" (FIG. 8) of the overall assembly. In some embodiments, the thickness may be ½ inch or less. The thickness may be reduced further as the outside diameters (OD) of the inlet port and outlet port 106 and 108 respectively reduces from the preferred ¼ inch. In embodiments where the integral filter assembly is between the patient and the device end of its respective cannula, the relatively small thickness "T" (FIG. 8) provides for an unobtrusive presence of the filter assembly, such by affixing the filter assembly to the garment on the patient's chest.

Figure 9:
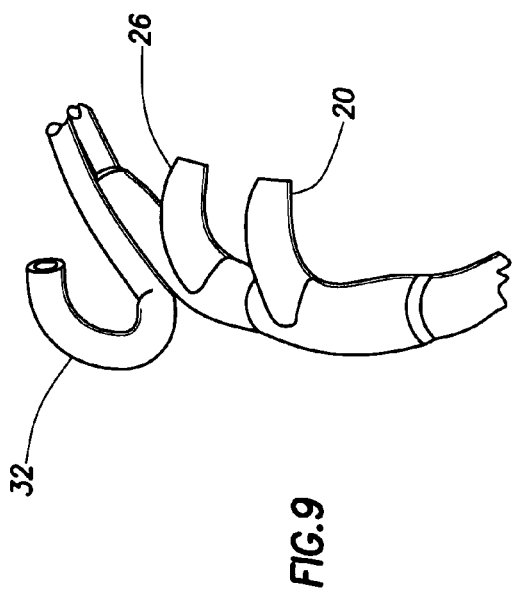
FIG. 9 illustrates, in greater detail, the relationship of the nasal prongs and oral interface in accordance with at least embodiments of the invention.

FIG. 9 illustrates in greater detail the relationship of the nasal prongs and oral interface in accordance with at least some embodiments of the invention. In particular, FIG. 9 shows right nasal prong 20, left nasal prong 26 and oral interface 32. As illustrated in FIG. 1, the right nasal prong 20 is placed in fluid communication with patient's right naris, the left nasal prong 26 is placed in fluid communication with the patient's left naris, and the oral interface 32 is placed in fluid communication with the patient's mouth. In accordance with at least some embodiments, the prongs 20, 26, as well as the oral interface 32 have a length at least as long as may be needed for any patient, and the prongs and interface may then be trimmed to precisely fit each particular patient. In some embodiments, the apertures of the nasal prongs are placed just below the nasal openings. In yet further alternative embodiments, the nasal prongs 20 and 26 may be removed completely and/or not provided, and in these embodiments an aperture into the respective tubings may be the mechanism by which the patient is fluidly coupled to the independent flow paths of the cannula. In yet further embodiments, a non-bifurcated oral tube may extend over each ear, merging below the patient's chin or behind the patient's head.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A cannula comprising:
   a first nasal tubing having a device end and an aperture end, wherein the cannula is configured to place the aperture end in fluid communication with a first naris of a patient;
   a second nasal tubing having a device end and an aperture end, wherein the cannula is configured to place the aperture end of the second nasal tubing in fluid communication with a second naris of the patient; and
   an oral tubing having a device end and an aperture end, and oral tubing mechanically coupled to at least one of the first or second nasal tubing, wherein the cannula is configured to place the aperture end of the oral tubing in fluid communication with a mouth of the patient;
   wherein the first nasal tubing, the second nasal tubing and the oral tubing are fluidly independent between their aperture ends and their device ends.

2. The cannula as defined in claim 1 wherein the oral tubing is coupled parallel along at least a part of the first nasal tubing.

3. The cannula as defined in claim 1 further comprising:
a first filter assembly in fluid communication with the first nasal tubing;
a second filter assembly in fluid communication with the second nasal tubing; and
a third filter assembly in fluid communication with the oral tubing.

4. The cannula as defined in claim 3 wherein each filter has functionality of at least one of: a hydrophobic filter; or a microbial filter.

5. The cannula as defined in claim 3 wherein the first, second and third filter assemblies are an integral assembly.

6. The cannula as defined in claim 5 wherein the integral assembly is fluidly coupled between the aperture and device ends of each respective tubing.

7. The cannula as defined in claim 5 wherein the integral assembly forms the device end of each respective tubing.

8. The cannula as defined in claim 3 further comprising:
wherein the first filter assembly forms the device end of the first nasal tubing;
wherein the second filter assembly forms the device end of the second nasal tubing; and
wherein the third filter assembly forms the device end of the oral tubing.

9. A cannula comprising:
a first nasal tubing, wherein the cannula is configured to place a patient end of the first nasal tubing in fluid communication with a first naris of a patient;
a first inline filter within the flow path of the first nasal tubing;
a second nasal tubing mechanically coupled to the first nasal tubing, wherein the cannula is configured to place a patient end of the second nasal tubing in fluid communication with a second naris of the patient;
a second inline filter within the flow path of the second nasal tubing;
an oral tubing, wherein the cannula is configured to place a patient end of the oral tubing in fluid communication with a mouth of the patient; and
a third inline microbial filter within the flow path of the second nasal tubing;
wherein the first and second nasal tubings are fluidly independent.

10. A respiratory air filter assembly comprising:
a first flow pathway comprising an inlet port and an outlet port fluidly coupled to a first cavity, the first cavity defined, at least in part, by an outer housing;
a second flow pathway comprising an inlet port and an outlet port fluidly coupled to a second cavity, the second cavity defined, at least in part, by an outer housing;
a third flow pathway comprising an inlet port fluidly and an outlet port fluidly coupled to a third cavity, the third cavity defined, at least in part, by an outer housing;
a first filter within the first cavity; and
a second filter within the second cavity,
a third filter within the third cavity;
wherein at least a portion of the outer housing defining the first cavity is mechanically coupled to the outer housing defining the second cavity, and wherein at least a portion of the outer housing defining the third cavity is mechanically coupled to the outer housing defining the second housing.

11. The respiratory air filter as defined in claim 10 wherein the respiratory air filter is configured to hold each filter in a plane substantially parallel to a plane defined by the inlet ports of the first, second and third air pathways.

12. The respiratory air filter assembly as defined in claim 10 wherein the outlet ports of the first, second and third air pathways define a plane, and the plane defined by the outlet ports is substantially parallel to a plane defined by the inlet ports.

* * * * *